(12) United States Patent
Harmon (10) Patent No.: US 6,512,986 B1
(45) Date of Patent: Jan. 28, 2003

(54) METHOD FOR AUTOMATED EXCEPTION-BASED QUALITY CONTROL COMPLIANCE FOR POINT-OF-CARE DEVICES

(75) Inventor: Kirk C. Harmon, San Ramon, CA (US)

(73) Assignee: Lifescan, Inc., Milpitas, CA (US)

( * ) Notice: Subject to any disclaimer, the term of this patent is extended or adjusted under 35 U.S.C. 154(b) by 0 days.

(21) Appl. No.: 09/751,570

(22) Filed: Dec. 30, 2000

(51) Int. Cl.[7] ............................................... G06F 19/00
(52) U.S. Cl. ........................................... 702/84; 702/81
(58) Field of Search ................................. 705/3; 702/84

(56) References Cited

U.S. PATENT DOCUMENTS

| | | |
|---|---|---|
| 5,199,439 A | 4/1993 | Zimmerman et al. |
| 5,430,833 A | 7/1995 | Terenghi |
| 5,633,166 A | 5/1997 | Westgard et al. |
| 5,845,255 A | * 12/1998 | Mayaud ........................ 705/3 |
| 5,937,364 A | 8/1999 | Westgard et al. |
| 5,941,820 A | 8/1999 | Zimmerman |
| 5,987,398 A | 11/1999 | Halverson et al. |

OTHER PUBLICATIONS

Westgard et al., A Multi–Rule Shewhart Chart For Quality Control in Clinical Chemistry, Clin. Chem. 27/3, pp. 493–501 (1981).

* cited by examiner

Primary Examiner—John S. Hilten
Assistant Examiner—Xiuqin Sun

(57) ABSTRACT

A computer-implemented method to process POC information for potential QC compliance issues. A system and method for implementation of traditional laboratory analyzer based QC compliance in point-of-care (POC) environments is disclosed. A specific system and method to analyze data from POC testing to identify when the testing exceeds the variation expected under stable operation (i.e., the testing is "out of control") is disclosed. This system and method is characterized by solving the QC compliance problem for POC devices by individuals not trained in traditional laboratory practices. This also provides the capability in real-time or near real-time to analyze POC testing information regarding the performance of each POC device, reagent kit (i.e., one kit per analyte tested) and/or lot, and operator so one can respond quickly to a particular device, reagent kit and/or lot, or operator that is not performing properly.

6 Claims, 8 Drawing Sheets

QC Compliance Review

Review

Exception date/time: 11/4/2000 4:09 PM

QC rule: Trend - High

Meter: ACU (1) - L7298AA00047

Test strip lot number: 728852A005

Start date: 10/31/2000      End date: 11/3/2000

Duplicate: No

Results:

| Date/Time | Location | Operator ID | Operator Name | Solution Lot.. | Result | Limits | Comments | Flags |
|---|---|---|---|---|---|---|---|---|
| 10/31/2000 4:32 PM | CH - ACU | 09675401 | | MF0271 | 348 | 243 - 365 | | NVO |
| 11/1/2000 2:46 PM | CH - ACU | 09817701 | Lyman, Peter | MF0271 | 340 | 243 - 365 | | |
| 11/2/2000 4:49 PM | CH - ACU | 07481301 | Mangum, Debra | MF0271 | 342 | 243 - 365 | | |
| 11/3/2000 4:47 PM | CH - ACU | 20207401 | Asare, Cynthia | MF0271 | 345 | 243 - 365 | | |

OK    Cancel —706    View Report —710    Help

FIG. 8

METHOD FOR AUTOMATED EXCEPTION-BASED QUALITY CONTROL COMPLIANCE FOR POINT-OF-CARE DEVICES

FIELD OF THE INVENTION

The present invention relates generally to quality control (QC) compliance monitoring and more specifically to a system (analytical testing process) for automated exception-based quality control compliance for point-of-care devices.

BACKGROUND OF THE INVENTION

All clinical laboratories in the United States must comply with the Clinical Laboratory Improvement Amendments of 1988 (CLIA '88). CLIA '88 has established the minimum standards for all laboratory testing, including specific regulations for quality control. Although CLIA '88 does nor explicitly recommend a method for determining when a system is out of control, the federal law does state that laboratories must:

perform control procedures using at least two levels of control materials each day of testing     establish written procedures for monitoring and evaluating analytical testing processes     follow the manufacturer's instructions for quality control To achieve the goal of quality control, including the precision and accuracy of test results, it is necessary to be able to detect errors within the system as soon as possible. Before designing an error detecting system, something must be known about the nature of the errors to be detected. Typically, the errors in a quantitative system are random errors and systematic errors.

Random errors are always present to a measurable degree in any system given a set of circumstances-glucose meters (the devices), operators, test strips (the reagent), and control solutions (the control material), for example. The amount of random error, sometimes referred to as precision, is usually measured by the standard deviation (SD) and the coefficient of variation (CV). The SD measures the scatter (for variability around the true value) in the data points (test results), while the CV is the standard deviation expressed as a percent.

The other type of error is systematic error. These errors, of which shifts and trends are included, occur in one direction away from the true value and are measured by using the mean. Accuracy is the term used when referring to how close a test result is to the true value.

Not only should the error detecting system be able to detect these two types of errors, but it should be able to tell us whether the error is random or systematic because this leads the analysis in a direction which is highly significant.

The manufacturer's stated QC ranges give an indication of where the mean and QC limits may be, but the manufacturer data is not considered an appropriate substitute for a mean and QC limits determined from the institution's own established data. Each institution should determine the performance of their measurement system and set an appropriate mean and QC limits for the controls based on their own data. New reagent and/or control material should be analyzed for each analyte in parallel with the reagent and/or control material currently in use.

The National Committee for Clinical Laboratory Standards (NCCLS) recommends that as a minimum, 20 data points from 20 or more separate runs be obtained to determine an estimate of mean and standard deviation for each level of control material. A run is typically defined in terms of a length of time or a number of samples analyzed. Better estimates of both mean and standard deviation can be achieved when more data is collected. Additionally, the more controls run, the easier it is to detect true changes in the measurement system.

It is important to include all valid data points attained with the selected collection method. For example, if values outside of 2 SD are not included in the data, an artificially small estimate of variability may be calculated.

If data collection is to be representative of future system performance, sources of variation that are expected and determined acceptable may be included during the data collection period. These may include multiple devices, reagent lots, multiple control material lots, and multiple operators to name a few examples.

The Gaussian distribution, or bell-shaped curve, is the most frequently used model when analyzing clinical data. Using the true standard deviation, statistical theory shows that 99.73% of the data will fall within ±3 SD of the mean, 95.44% will fall within ±2 SD of the mean, and 68.26% will fall within ±1 SD of the mean for each level of control material. (Standard deviation estimates from actual data may vary from the true standard deviation.)

After determining the mean and SD of a measuring system, many institutions will decide to set control limits as some multiple of the SD around the mean, for example, at ±2 SD or ±3 SD to determine when a system is out of control. The problem with this single-rule method is that even if there is no change in the performance of the system and everything is operating as expected (system is in control), you will still have 4.56% (100−95.44=4.56) of values fall outside the ±2 SD limits. These points are considered false rejections, and the more data points you collect, the higher the number of false rejections encountered. Thus, while the ±2 SD offers a very sensitive method to detecting a change, is also presents a real problem-a high rate of false rejection.

Multirule quality control methods use a combination of control rules to more accurately decide whether analytical runs are in control or out-of-control. Unlike the 2-SD or 3-SD limit rules described above, the Westgard Multirule Procedure (Westgard 1938) uses six different control rules to judge the acceptability of an analytical run. The advantages of a multirule QC method are that false rejections can be kept low while at the same time maintaining high error detection.

The following summarizes the individual Westgard 1938 control rules:

| Rule | Definition |
| --- | --- |
| $1_{2s}$ | One result falls outside 2 SD. |
| $1_{3s}$ | One result falls outside 3 SD. |
| $2_{2s}$ | Two consecutive results fall outside 2 SD on the same side of the mean. |
| $R_{4s}$ | The range of two results is greater than 4 SD. |
| $4_{1s}$ | Four consecutive results fall outside 1 SD on the same side of the mean. |
| $10_x$ | Ten consecutive results fall on one side of the mean. |

To perform multirule QC, start by collecting control data and establish the means and SDs for each level of control material. If performing QC manually (plotting and interpreting data without the use of a computer program), create a Levey-Jennings chart and draw lines at the mean, ±1 SD, ±2 SD, and ±3 SD.

In manual applications, the $1_{2s}$ rule should be used as a warning to trigger application of the other rules. It indicates that one should look carefully before proceeding. Stop if the $1_{3s}$, rule is broken. Stop if the $2_{2s}$, rule is broken. Stop if the $R_{4s}$ rule is broken. Often the $4_{1s}$, and $10_x$ rules must be used across runs in order to get a sufficient number of control measurements needed to apply the rules.

A software program should be able to select the individual rejection rules on a test-by-test basis to optimize the performance of the QC procedure on the basis of the precision and accuracy observed for each analytical method and the quality required by the test.

SUMMARY OF THE INVENTION

A computer-implemented method to process point-of-care (POC) information for potential QC compliance issues. A system and method for implementation of traditional laboratory analyzer based QC compliance in POC environments is disclosed. A specific system and method to analyze data from POC testing to identify when the testing exceeds the variation expected under stable operation (i.e., the testing is "out of control") is disclosed. This system and method is characterized by solving the QC compliance problem for POC devices by individuals not trained in traditional laboratory practices. This also provides the capability in real-time or near real-time to analyze POC testing information regarding the performance of each POC device, reagent kit (i.e., one kit per analyte tested) and/or lot, and operator so one can respond quickly to a particular device, reagent kit and/or lot, or operator that is not performing properly.

The disclosed invention builds upon the QC control testing and warning/lockout functionality currently performed and supported by many POC devices. Typically, QC enforcement is specified by a POC administrator (a.k.a. coordinator) so that required QC test(s) must be performed at designated intervals to avoid a QC warning or lockout. These POC devices provide a method to warn/flag or lockout patient testing if any required QC test fails (i.e., not within expected QC limits) or is not run as scheduled. Additionally, the disclosed method builds upon connectivity solutions which have become industry standard for POC devices. These solutions allow for the transfer of QC and patient test results from POC devices, the transfer of configuration information to POC devices, and the transfer of Patient (and QC) test results to laboratory and/or hospital information systems.

In summary, the present system and method provide traditional laboratory analysis based QC compliance processing in POC environments. The unique characteristics of a POC environment include multiple and possible widely distributed testing devices (typically with limited processing capability); utilizing multiple reagent kits and/or lots; and, use by multiple operators to perform various analytical testing at or near the site of patent care.

The invention provides automated QC compliance checking to verify POC testing is performing properly (i.e., a method to monitor and evaluate the QC test results of a POC environment and to identify and alert the POC administrator (s) when the testing exceeds the variation expected under stable operation). Additionally, to automate the identification of the specific cause of the variation (e.g., device(s), reagent kits and/or lot(s), and/or operator(s)); the current industry standard is a manual review of QC compliance and outlier reports and manual intervention when system is found to be "out of control".

The invention provides exception-based QC compliance for POC environments to ensure timely notification and response to "out of control" POC testing, to improve the quality of patent testing performed at or near the site of patient care. Additionally, to reduce the need and the time to manage POC information (i.e., timely access to accurate and complete QC information is critical for cost effective quality health care delivery).

The invention defines rules for detecting random and systemic errors within QC test results (i.e., QC compliance settings which are similar to traditional Westgard 1938 rules) and to automatically log the QC compliance settings and/or changes.

The invention detects potential inaccurate patient results and optionally holds for review any POC collected patient results when associated with QC compliance exceptions (i.e., optionally delay the reporting and/or transfer to an information system of potential inaccurate patient results).

The invention logs and maintains QC compliance issues (i.e., exceptions to defined rules).

The invention alerts POC administrator (a.k.a. coordinator) to potential QC compliance issues (possible options include status display, electronic mail, faxing, and paging). (See data flow #7).

The invention clears QC compliance alerts when reviewed by POC administrator (a.k.a. coordinator).

The invention defines rules for detecting and optionally disabling the cause of the variation (e.g., number of QC compliance issues within a specified time frame for devices, reagent kits and/or lots, and/or operators) and to automatically log the QC compliance settings and/or changes.

The invention automatically disables questionable POC devices (i.e., a feedback loop built upon connectivity solutions and device configuration). Additionally, the ability to automatically remove from use (via device configuration) any "out of control" reagent kits and/or lots, and/or operators.

The invention releases for or stops from reporting and/or transfer to an information system patent results associated with QC compliance exceptions (following the review of associated QC compliance exception(s)).

The invention provides automated access (e.g., browse) to current and reviewed QC compliance exceptions with detailed QC compliance reporting (e.g., Levey-Jennings chart and associated statistical analysis) to support accreditation requirements and continual improvement in the quality of care provided by POC testing. (See data flow #7, #8, #9, and #12).

The invention supports automated accreditation validation (e.g., CAP or JACHO) via logging of QC compliance settings, QC compliance exceptions, and the review of QC compliance exceptions, and storing the above for review by the administrator and/or an auditor.

Point-of-care, or near the site of patient care, testing is a technological innovation that has demonstrated the potential for improving patient care (i.e., improves the quality and outcomes of care while decreasing cost and length of stay for patients), assuming accurate and precise patient results are obtained in near real-time. The ultimate goal of quality control (QC) compliance is to ensure accurate and precise patient results whether generated by point-of-care (POC) devices or performed by traditional laboratory analyzers. However, to ensure POC testing generates accurate and precise patient results, an automated method to monitor and evaluate the QC test results of a POC environment, and to identify and respond when the testing exceeds the variation expected under stable operation is required. Additionally, to ensure timely notification and response to "out of control" POC testing, an exception-based method is required.

Other features and advantages of the inventive system will be apparent to a person of skill in this art who studies the following description of an exemplary embodiment.

DETAILED DESCRIPTION OF A PREFERRED EMBODIMENT

Figure 1:
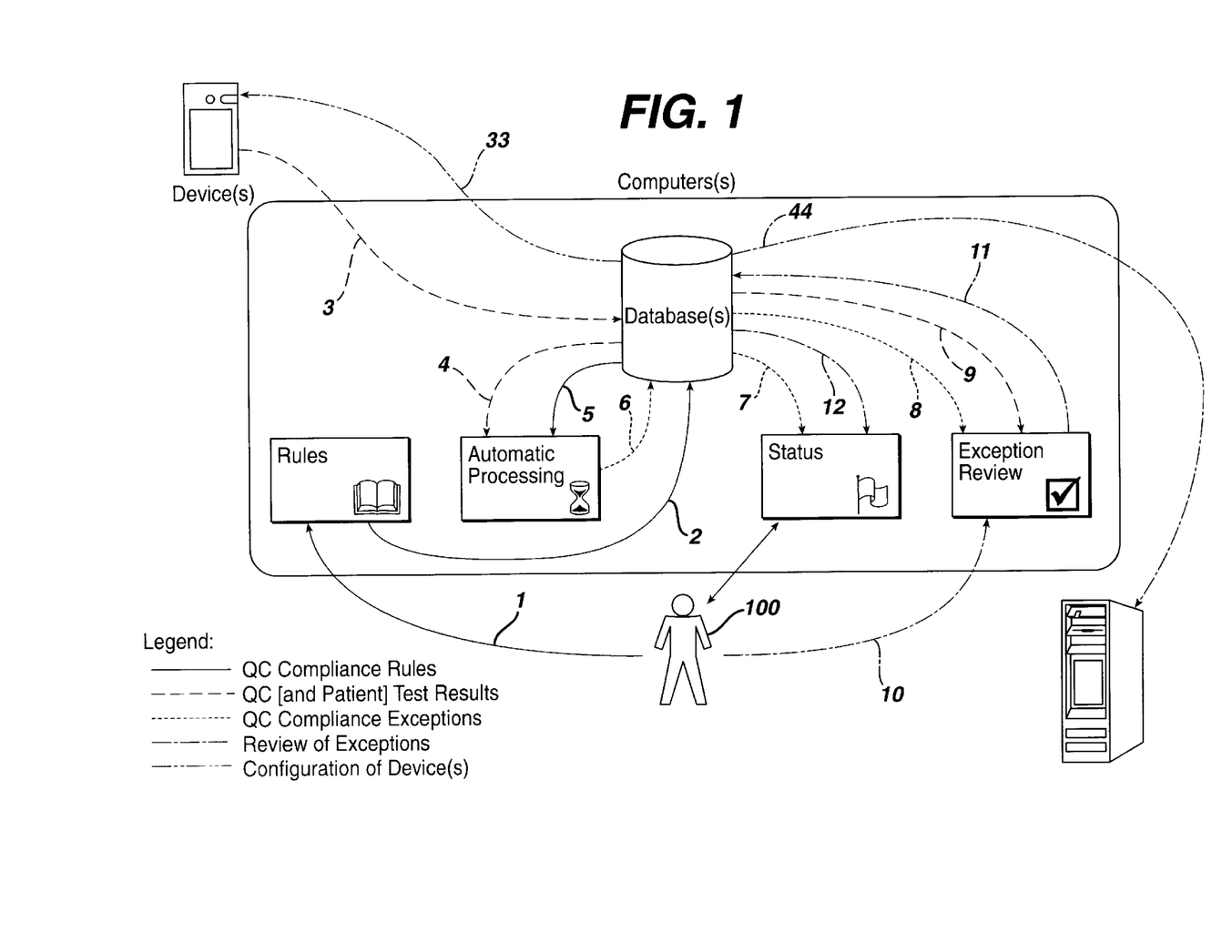
FIG. 1 is a diagram and method of the system of this invention.

A preferred embodiment of this system and method is depicted in FIG. 1. The data paths or steps (numbered from 1 to 12) are preferably conducted in the specific and unique order illustrated and outlined within this disclosure. These data flows are identified as QC compliance rules, QC test results (and optionally associated patient test results) from POC devices, QC compliance exceptions, and review of exceptions. Two additional data flows, configuration of device(s) and patient test results (and optionally associated QC test results) to information system(s), while elements of this disclosed method, are not sequenced by the disclosed method. The sequencing of these additional data flows may vary based upon configuration of the computer-implemented method. Furthermore, embellishment or addition of data flows to the system and method disclosed can be shown to not change the nature and utility of this method. The components of the computer-implementation (i.e., rules, automatic processing, status, and exception review as illustrated) are elements of the disclosed method; however, a computer-implementation may combine and/or decompose these elements.

The present method and system disclosed is used to monitor the use of and the quality of the readings taken from glucose meters. These meters are utilized for the majority of all point-of-care testing done in this country with the total testing volume amounting to several hundred million tests per year. However, the invention can as well be used with any POC device.

FIG. 1 is a schematic diagram illustrating the interaction between the basic units of the system, including the software controlled elements as well as the points in which human intervention is either available or required. The rules, which are basically QC compliance rules and which are well-known in the field of quality control, are entered as step 1 (the numbers represent both steps and data paths) by the administrator 100. These are the rules, typically similar to traditional Westgard 138 rules, by which random and systemic errors within QC results. Additionally there are rules to decide when to disable POC components. One of the technical advances and approved efficiencies provided by this invention is that a single administrator from any part of the country or even another country, can establish, in some instances, the set of rules by which the quality of the reading taken on numerous point-of-care devices is judged and the response to be made. This approach dramatically reduces the cost and simplifies the function of the overall system. Furthermore, by using this approach, the same set of rules is applied to judge the quality of the operation of the POC devices throughout the entire system, without the regional or local distinctions which would inevitably enter into a more locally based system. The set of rules are adopted to look for both random and systemic errors.

The rules, which will be discussed further below, are then stored in step 2 in the database 104, which again is central and common to the entire system and supports all of the POC devices. The database 104 maintains the rules and stores all of the information from the devices because such storage is necessary in such a highly distributed operating environment. Use of such centralized storage also improves the efficiency and level of simplification of operation of the overall business system. One of the basic driving forces behind the adoption of this system is that in order to collect medical insurance reimbursement for tests, and/or maintain accreditation for the institution, or for review by a doctor or POC administrator, it is required that the system and/or the test be periodically demonstrated to produce accurate results. For this reason, it is necessary to maintain detailed records of the tests that have been run. The significance of storing the rules in the central database where all test information is stored, is that an auditor must know exactly what rules were being used and standards applied at the time each test set was performed. Otherwise, a very relaxed set of rules could be utilized, creating a false impression of a high level of reliability.

The next 3 steps or data paths are established to detect potentially inaccurate patient results and optionally hold for review any POC collected patient results that are associated with a QC compliance exception. That is, this system supports delaying the reporting and/or transfer of potentially inaccurate patient results to any external laboratory or hospital information system (LIS or HIS).

The next step 3 is the data transferring from the POC device 108 to database 104. As noted above, these POC devices 108 are typically microprocessor based so that they can communicate across an appropriate interface with the database 104. In this specific example, the POC device is a glucose meter which is currently the most common type of POC device.

The POC device 108 typically includes a laser bar code reader, a data port for communications, and the like. Its purpose is basically to take reagent strips or cartridges and read the result of any chemical reaction which has been recorded by or monitored by the test strips or cartridges. The device 108 typically will store identifiers for hundreds to thousands of different operators, and hundreds to thousands of results, each result potentially performed by a different operator using different reagent kits and/or lots. Of course, it is apparent that this system is not usable solely with such a POC device, but rather can be adapted to be used with any POC device or even with different POC devices.

Each POC device would need to be identified as to its type, and associated with a set of rules input by the administrator 100 and stored in the database 104. The importance of setting up the system, as defined here, is that one of the essential elements of POC devices is that a nurse or technician can run the test, evaluate the test, and then potentially immediately treat the patient. However, the use by different operators and the rapidity with which the test is given and evaluated, can also easily lead to compromises in quality, which must immediately be detected. To address this problem, as well as maintain these standards, quality control tests are periodically run through the POC devices 108. Such tests produce results which can be compared to fixed standards to determine that the POC device is, in fact, operating correctly and providing accurate readings. In the absence of running such standardized tests, the user could either generate errors on either side of correct readings, or could produce a long-term trend away from correct readings. Therefore, the device 108 stores each test result associated with a particular operator and a particular reagent lot as well as the results of the standardized test, and on a periodic (to "real-time") basis transmits these results to the database 104 for storage. The period can be as short as seconds or minutes, or even to every week or month.

There is also, of course, a data flow from the database back to the device 108 represented by the line 33. This represents the fact that as the database 104 accepts and the system monitors, as will be described below, the results of the system monitoring may be used to disable a questionable POC component via path or step 33. The system and method thereby incorporates the ability to automatically remove from use (via device configuration) any "out-of-control" devices, kits and/or reagent lots, and/or operators.

The data sent back on path 33 could convey a message to the operator that the device was now operating outside of standards; or the path could be used to lock out a particular operator or a particular class or run of reagent strip. In sum, at this stage, and by the processing which will now be described, it is possible to create long-term storage of the data and provide feedback which could potentially lock out either an operator, a reagent, or a particular POC device from performing analytical testing pending review. It should be further noted that in discussing the remaining data flows and steps which appear on the diagram of FIG. 1 (aside from path 44), that the sequence represented by the numbers is a preferred sequence so that the data is properly analyzed, exceptions generated, and standards for judging the quality of the tests being run are maintained.

The two flows or steps 33 and 44 can generally occur at any time in the sequence. Of the next two steps, step 4 is the conveyance of the rules associated with the data comprising the QC rules, and step 5 is the transfer of QC results from the database for automatic processing. The processing system 110 comes into play at this point and must process the data by comparing statistical calculations performed on the data to the rules. The processing which now occurs will look for both random and systemic errors by looking at the periods of time when it was collected and looking for deviations or trends from expected standards. An example of setting up the system for looking for standard deviation (random error), and trends (systemic errors), using some unique and specially simplified interfaces to enhance the quality and accuracy of the POC data will be described below. Mean and standard deviation values are calculated, typically for a particular device and/or operator and/or reagent. As the values are calculated by the automatic processing system 110, any calculated value which falls outside an expected range, is reported as an exception and stored to the database 104 during step 6. In this way, all QC compliance issues (i.e. exceptions to defined rules) are logged and maintained.

At this point, pursuant to step 7, detection or logging of an exception must be noted by creating a status report to the administrator(s). This status report may consist of a flag warning or a message given to the administrator. The message, in fact, can take the form of a page, an e-mail, a fax, or the like. The important fact is that the administrator (s) is, in fact, notified of the existence of an exception to defined standards of operation. It is at this point that information may also be conveyed 44 to the HIS or LIS where the test was conducted, or the hospital or doctor that authorized the test. The step 44 can comprise an e-mail, a page, or the like, being conveyed to the doctor saying that attention should be paid to the results of the test which has just been logged into the database 104.

Therefore, while the data flow 44 can occur at many places, it may occur following step 6 where the exception has been logged.

The next step required is step 8, which is the exception review, 130. At this step, the exceptions which have been statistically identified and logged, typically in conjunction with the QC and optionally patient test result(s) which have also become a part of the exception review at step 9. This is done in conjunction with the administrator at step 10 who can now review the screens which log and show the exception(s) and the QC and patient test result(s). The administrator is required to review the results of steps 8 and 9 and may optionally put comments into the system at step 10. Thus these steps 8, 9 and 10 are combined to review all QC compliance issues, and also patient results associated with QC compliance exceptions. This is the point at which the data is analyzed statistically, and charts such as a Levey-Jennings chart may be generated to demonstrate how the data compares to accepted forms.

At step 10, the administrator can add a comment which may in fact clear the data for reporting in path 44; as the administrator may, on manual review of the data, conclude that, in fact, the operation was properly carried out. The administrator may also, after review of the QC and optionally patient test results, add comments to the exceptions which are generated. These actions, optional comments, and choices, to accept patient or test results are stored in the database via path or step 11. The system thereby gives the administrator the opportunity to review QC compliance issues. It further gives the administrator the opportunity to have patient results associated with QC compliance exceptions withheld from reporting and/or transfer to an information system.

The data path 12 represents the method step which clears automatically any status flags or QC compliance alerts after review by the POC administrator(s) 100.

Finally, after all other data paths have been executed, then the data path or step 44 discussed above can be executed allowing the release or a stop placed on reporting of patient results from the device 108 to an information system.

The method and system described herein further provides along the path 33 an approach for automatically disabling questionable POC components. This step and apparatus provides the ability to automatically remove from use by way of device configuration over data path 33 any out of control devices, reagent lots and/or operators. The method and system described above further supports automated accreditation validation by logging all QC compliance settings, compliance exceptions, and a review of QC compliance exceptions. This is supported especially by the data paths 2, 6, 11 and the associated systems and data storage regions.

The above method and system also provide via the data flows and data paths 7, 8, 9, and 12, automated access (e.g. browsing) of current and reviewed QC compliance exceptions with detailed QC compliance reporting, e.g. Levey-Jennings charts and associated statistical analysis. This supports accreditation requirements and continual improvement in the quality of care provided by POC devices. Some details of the operation of an exemplary system will be described below.

In the exemplary embodiment to be described below, meter interface settings allow you to set multirule quality control criteria for all control results uploaded from the glucose meters. The implemented exemplary approach takes advantage of the basic principles of the Westgard 1938 rules, while allowing one to customize the rules for their needs. Select the Standard deviation rule and/or the Trend rule, then enter the specific parameters for each rule. The Westgard 1938 $1_{3s}$ and $2_{2s}$ rules are the basis for the Standard deviation rule; while the Westgard 1938 $4_{1s}$ and $10_x$ rules are the basis for the Trend rule (established settings and running values respectively). It is possible to implement multiple Standard deviation and Trend rules, to implement rules across multiple meters, devices and/or reagents and/or control solution types.

When a compliance rule is broken, an exception is created and a warning symbol appears on the QC Compliance icon at the software's Status tab. A notification is posted of one Standard deviation rule exception and/or one Trend rule exception per upload for each meter/test strip lot/control solution type combination. Upon reviewing the exceptions, all comments as well as any changes you make to the rules are logged in the Activity Log.

To monitor QC compliance, it is necessary to establish the QC rules to be used, and it is necessary to decide how closely to monitor QC results. One may want to set the rules more leniently to warn of an exception that most likely suggests a problem with the system. Or, one may set the rules more stringently so that a warning is set to look at the data, even though the exception is probably a false rejection.

The system is typically set to warn or lock out operators from testing when QC results fall outside the established ranges- typically these ranges are set to ±2 SD, but one may customize them appropriately for any institution. This meter (i.e., POC device) configuration setting corresponds to the Westgard 1938 $1_{2s}$ "warning" rule. With this mechanism in place, one option when setting compliance rules may be to set the meter to warn that the rule is broken, then set tight compliance rules to monitor any exceptions that occur beyond the $1_{2s}$ rule. Another possibility may be to set the meter to lock out operators at the $1_{2s}$ rule, then set loose compliance rules, as no patient tests can be performed when the meter is locked.

Any changes made to the QC Compliance rules are logged in the Activity Log within the database.

The sequence herein, which was detailed above, may be summarized as follows:
1. An administrator selects the Standard deviation rule and/or the Trend rule, then enters the criteria for each.
2. The compliance rules are stored in the database and logged in the Activity Log.
3. QC test results are uploaded from the meters to the computer and stored in the database. The compliance rules are applied to the QC test results. The information is processed. If an exception occurred, the administrator is notified via the warning symbol at the software's Status tab.
5. The administrator reviews each exception and optionally views the QC Compliance report, then enters comments, if applicable.
6. The reviewed exceptions (and comments) are stored in the database.
7. When all current QC compliance exceptions are reviewed, then the warning at the Status tab is cleared.

Figure 2:
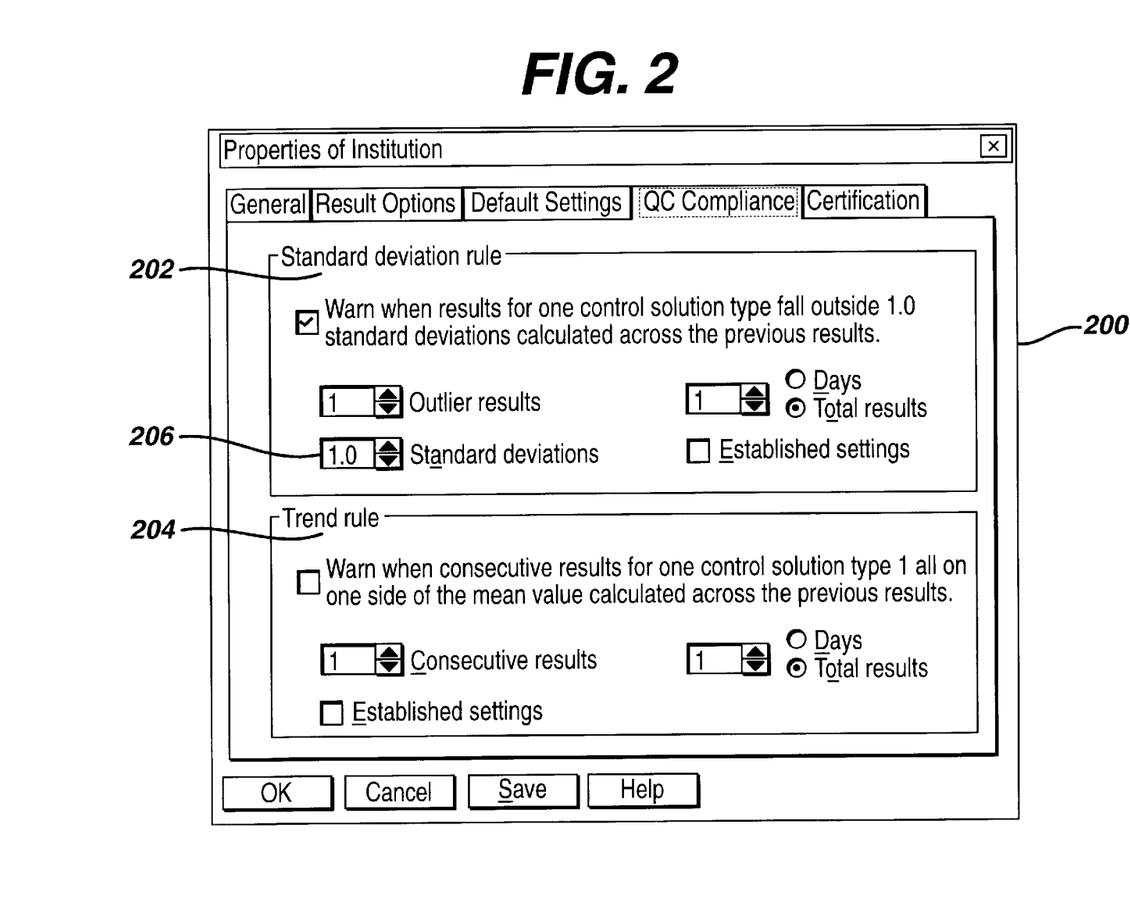
FIG. 2 illustrates an exemplary interface for setting the rules.

The initial setup for any institution uses the screen FIG. 2.
1. Using the screen 200, select the rule(s) you wish to use-Standard deviation 202 rule and/or Trend 204 rule.
2. Enter the variables which determine how lenient or stringent you want your QC compliance settings to be.
3. Select Established settings if you want to set your own mean and SD values. If you do not select Established settings, the software calculates a running mean and SD for the Standard deviation rule and a running mean for the Trend rule.

The software uses the standard deviation index (SDI) 206 to calculate the standard deviations. The standard deviation index is calculated using the following equation:

$$SDI = \frac{result - mean}{SD}$$

Figure 3:
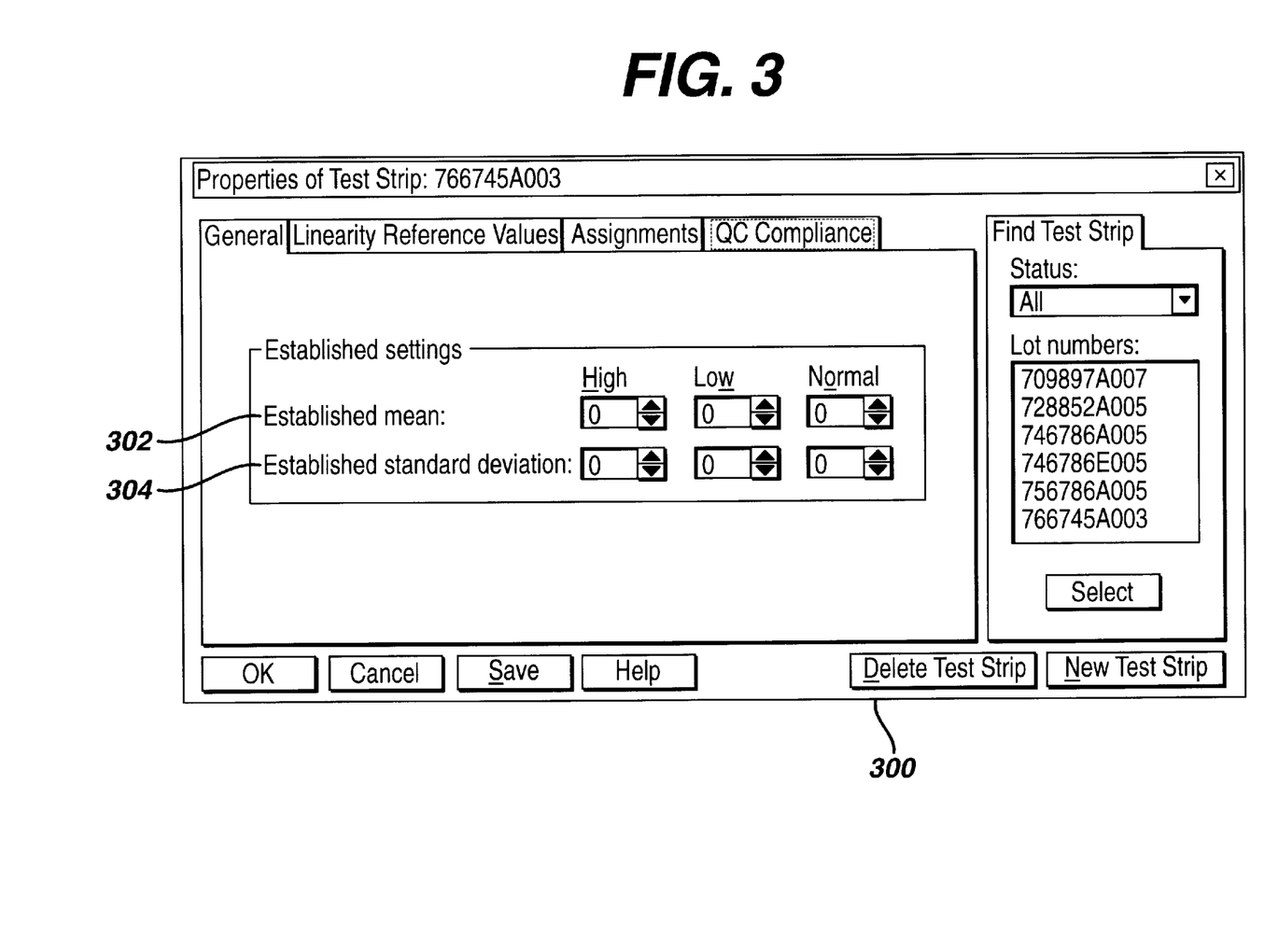
FIG. 3 illustrates an exemplary interface for setting properties of a test strip (reagent) for the QC limits.

If you select Established settings, proceed to the test strip properties interface 300, FIG. 3, to enter mean 302 and SD 304 values for each control solution type used by your institution. If you do not set these values, the system defaults to a running mean and standard deviation for the standard deviation rule and a running mean for the Trend rule.

Standard Deviation Rule

The standard deviation rule is selected to look for random errors in the testing procedure. The standard deviation rule warns when a specified number of results for one control solution type fall outside a specified number of standard deviations (SDI), either across a specified number of days or number of results. To implement this function it is only necessary to enter the values for the number of outliers, the number of standard deviations, and whether the study is across a number of days or a total number of results.

Once you enter the variables, you may choose to select Established settings, then enter your own customized values for mean and SD for each control solution type. If Established settings are not selected, the software calculates a running mean and SD for each result (over the number of days or total tests results that you select).

Figure 4:
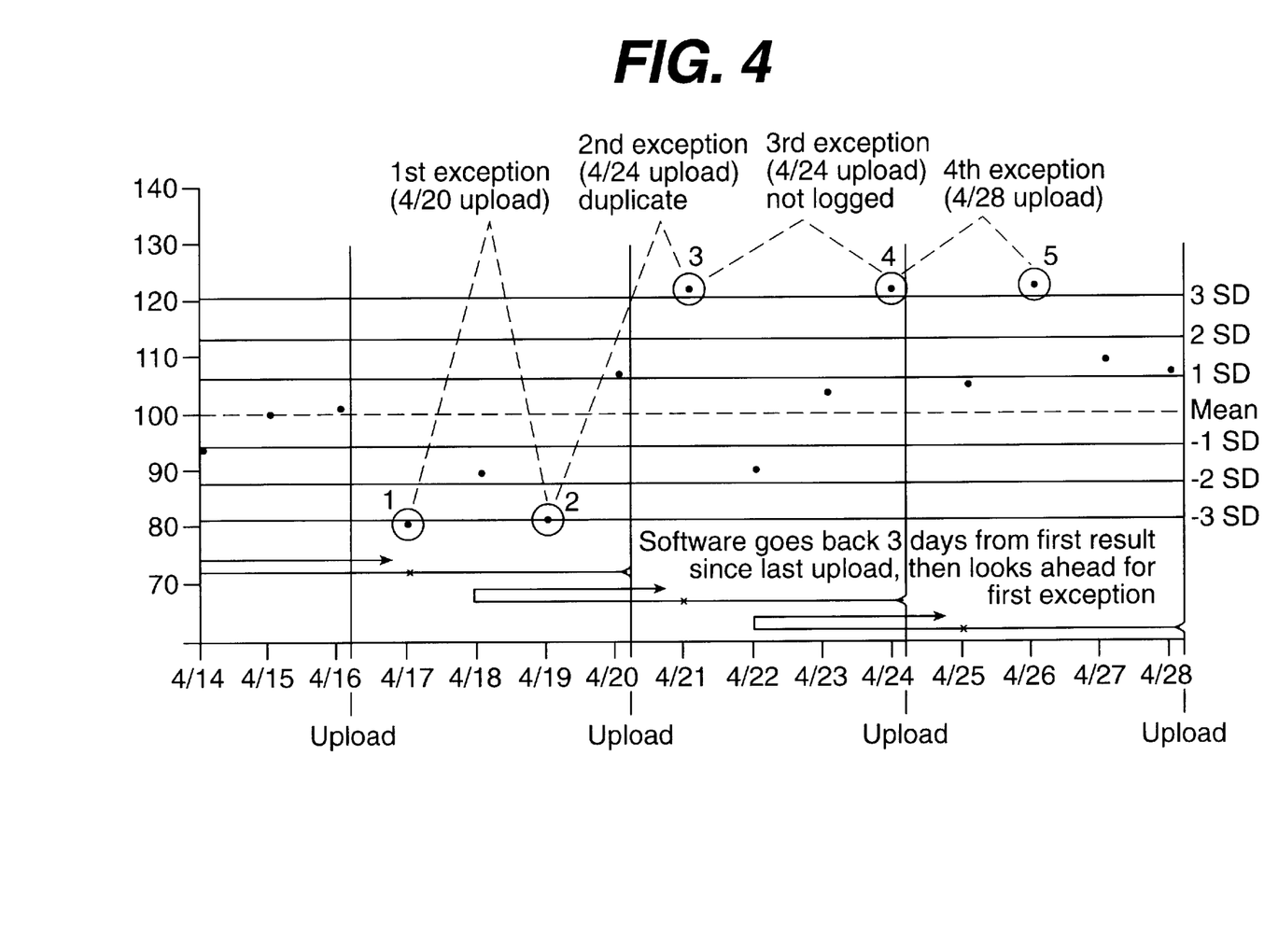
FIG. 4 is an example of a Standard Deviation Rule Exception (two results outside ±2.85 SD across three days).

An Example (with Established settings) is given in FIG. 4.

Criteria is set to 2 outliers, 2.8 SDs, across 3 days-Established settings is selected; therefore, one must enter values for mean and SD (assume 100 for mean and 7 for SD).

The Administrator will be warned every time 2 results for a control solution type fall outside ±2.8 SD from the mean. Upon upload, the software looks at the first result since the last upload, then goes back in time 3 days and begins looking towards the present for the first exception. Only one SD rule exception is logged per upload for each meter/test strip lot/control solution type combination.

Upload—QC Compliance Exceptions Detected
4/16 Insufficient Data Points
4/20 Exception Detected The software starts at the first result since the last upload (4/17 result), goes back 3 days to the 4/14 result, then looks to the present for an exception. One outlier is found on 4/17, a second is found on 4/19. Two outliers that fall ±2.8 SD from the mean and occur within 3 days satisfies the SD rule criteria.

4/24 Exception Detected (Marked as Duplicate)

The software starts at the first result since the last upload (4/21 result) goes back 3 days to the 4/18 result, then looks to the present for an exception. An outlier is found on 4/17, a second is found on 4/21. Two outliers that fall ±2.8 SD from the mean and occur within 3 days satisfies the SD rule criteria. Because the 4/19 result was included in a previously logged exception, the software marks this exception as a duplicate.

NOTE: Once an exception is found, the software stops looking even though another exception exists in the 4/21 and 4/24 results.

4/28 Exception Detected

The software starts at the first result since the last upload (4/25 result), goes back 3 days to the 4/22 result, then looks to the present for an exception. One outlier is found on 4/24, a second is found on 4/26. Two outliers that fall ±2.8 SD from the mean and occur within 3 days satisfies the SD rule criteria. Because the 4/19 result was included in a previously logged exemption, the software marks the exception as a duplicate. If the software detects the same results as part of another exception, the second exception will be marked "duplicate".

NOTE: Because the 3rd exception (as labeled on the graph) was never logged, the 4th exception is not marked as a duplicate.

Trend Rule

Select the Trend rule to look for data trends caused by systematic errors—problems with a meter, test strip lot (reagent), or an operator who may not be performing the test correctly. The Trend rule warns Administrator 100 when a specified number of consecutive results for one control solution type fall on one side of the mean, either across a specified number of days or a number of results (or ±1 SD from the mean if you select Established settings). Enter the values for the number of consecutive outliers, and look across a number of days or a total number of results.

Once you enter the variables, you may choose to select Established settings, then enter your own customized values for mean and SD for each control solution type. If you choose not to select Established settings, the software and system calculate a running mean for each result (over the number of days or total test results that you select).

NOTE: A standard deviation value is not used when you do not select Established settings (i.e. when a running mean is calculated)—the consecutive outliers may fall anywhere on the same side of the mean.

Figure 5:
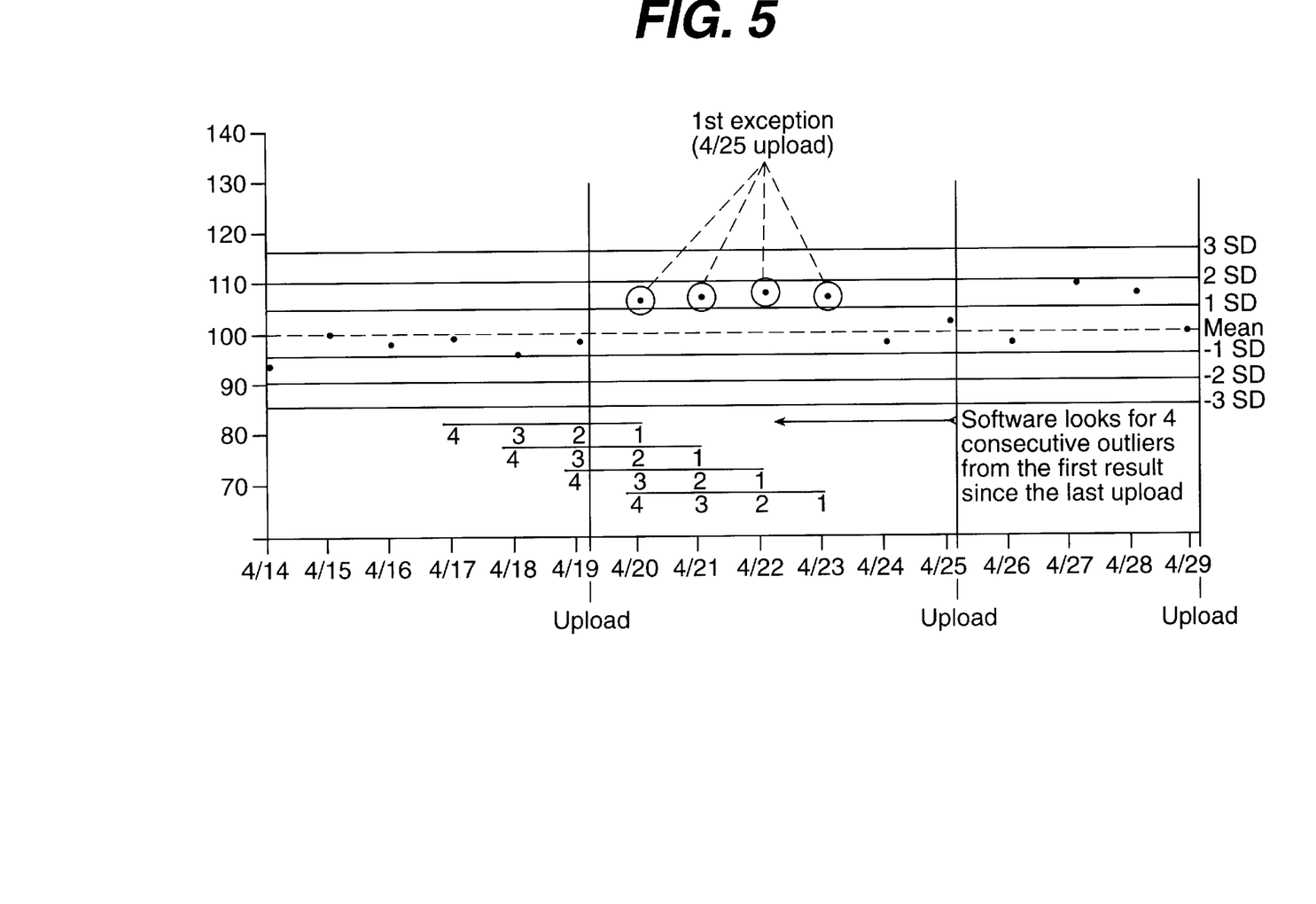
FIG. 5 is an example of a Trend Rule Exception (four consecutive results on one side of the mean).

An example (with established settings) is illustrated in FIG. 5 of a Trend Rule Exception, as described below.

Criteria is set to four consecutive outliers. Established settings is selected; therefore, you must enter values for mean and SD.

NOTE: The software uses the Total results or Days entered at the QC Compliance tab only when a running mean is calculated.

The Administrator will be warned every time 4 consecutive results for a control solution type fall outside ±1 SD from the mean. Upon upload, the software looks at the first result since the last upload along with the previous three results. If an exception is not found, the software shifts the four-result window ahead one result to continue looking for an exception. Only one trend rule exception is logged per upload for each meter/test strip lot/control solution type combination.

Upload—QC Compliance Exceptions Detected

4/19 No Exception Detected

4/25 Exception Detected

The software looks for four consecutive outliers beginning with the first result since the last upload (4/20 result) and including the previous three result. As the software continues to look ahead, is detects four outliers from 4/20 to 4/23. Four consecutive outliers that fall ±1 SD from the mean satisfies the Trend rule criteria. Once an exception is found, the software stops looking.

4/29 No Exception Detected

The software looks for four consecutive outliers beginning with the first result since the last upload (4/26 result) and the previous three results. The software finds only two outliers on 4/27 and 4/28, but no exception.

Reviewing OC Compliance Exceptions

Figure 6:
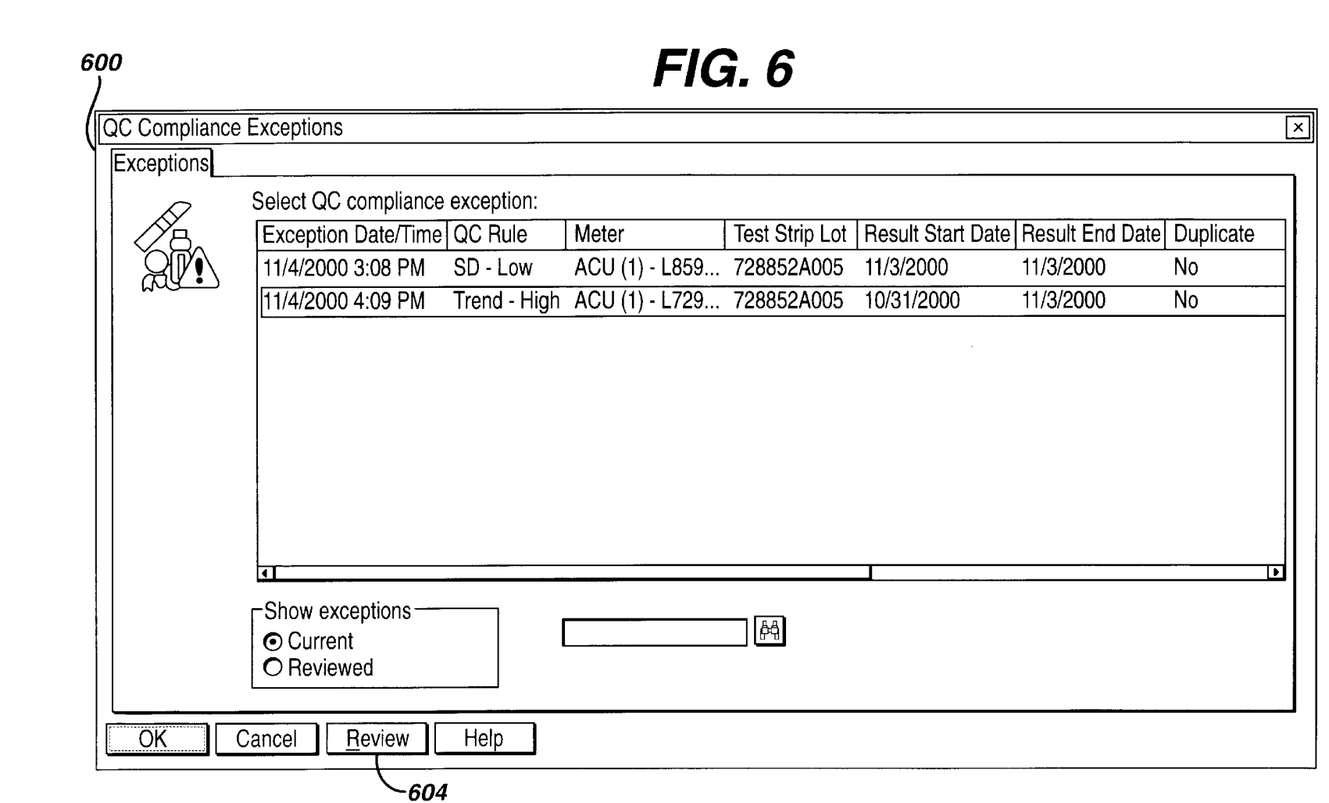
FIG. 6 is an example of an interface displaying compliance exceptions.

When a QC compliance rule is broken, an exception is created (FIG. 6). The software warns the Administrator by displaying a warning symbol 600 on the QC Compliance icon located on the Status tab. Click the warning symbol to display a list of exceptions.

Click the warning symbol on the Status tab to display a list of all exceptions since the last upload and any previous exceptions not yet reviewed and cleared.

At each upload, it is possible to get one exception per meter/test strip lot/control solution type combination for the Standard deviation rule and one exception per meter/test strip lot/control solution type combination for the Trend rule if you select both rules.

If you want to see the details of an exception, select the exception, then click Review 604. It's up to the system administrator to review the details of the exception, determine the most likely cause, and add optional comments, before clearing the exception.

Because each exception corresponds to a meter/test strip lot/control solution type combination, it is important to look at all exceptions collectively to further analyze the data. For example, are there multiple trend rule exceptions that are associated with the same test strip lot—indicating that a test strip lot may be the problem? Or, do the meter test comments, associated with the result of an SD rule exception, indicate that the operator used the wrong control level? Are the results from a particular operator consistently out of range? This can be done using the screen of FIG. 7 and calling up 706, the reviewed exceptions.

Once the administrator has reviewed the exception and optionally entered comments, the exception is cleared.

Figure 7:
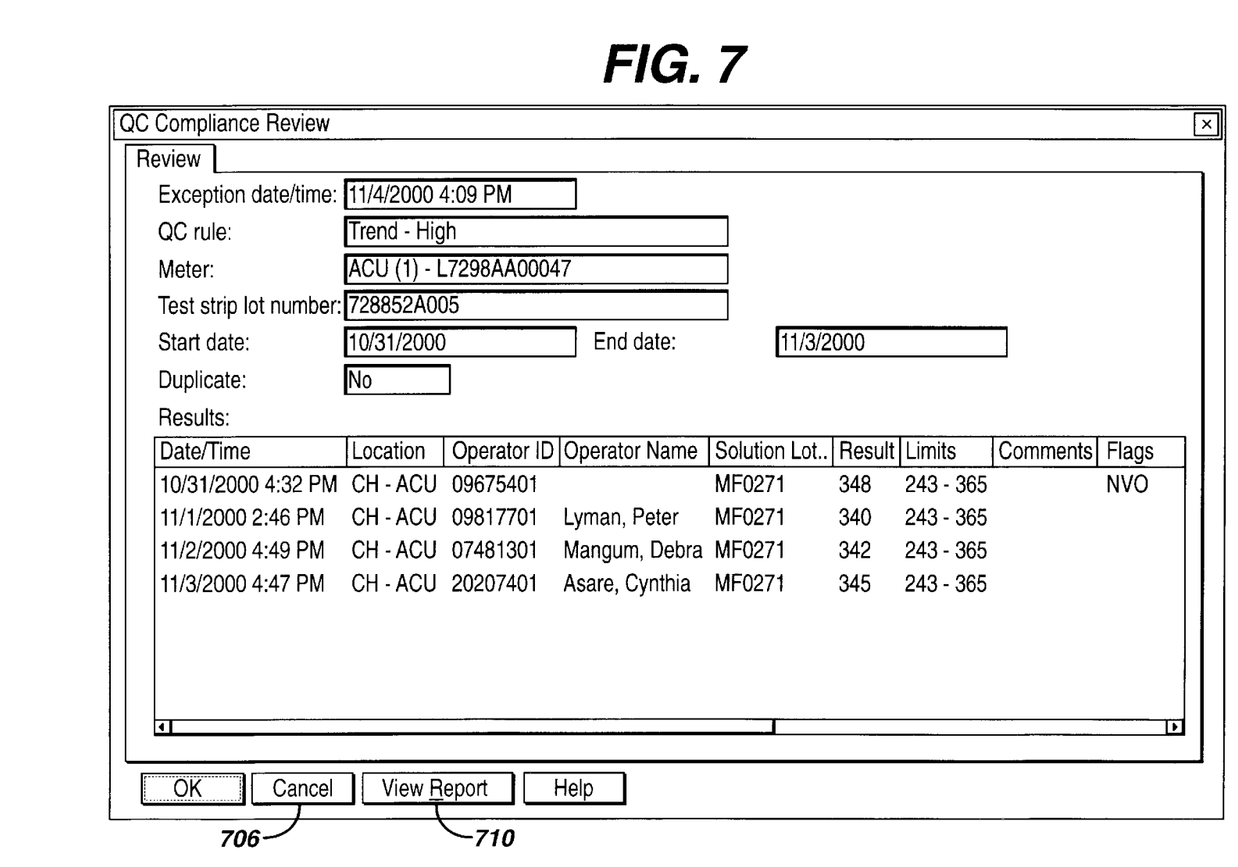
FIG. 7 is an example of an interface displaying details of a compliance exception.

An exception can be cleared at this point from the details sheet. Or, the QC Compliance Report can be displayed by clicking View Report 710.

OC Compliance Report

The QC Compliance Report includes a Levey Jennings-type chart showing all data points from (the first day of the week on which the first outlier occurred) the first outlier in the exception to the present time (or up to a maximum of 3 months). (See FIG. 8) Although the software records only the first exception that was found, if any additional exceptions occurred in the time period, you will be able to see them within the chart.

Figure 8:
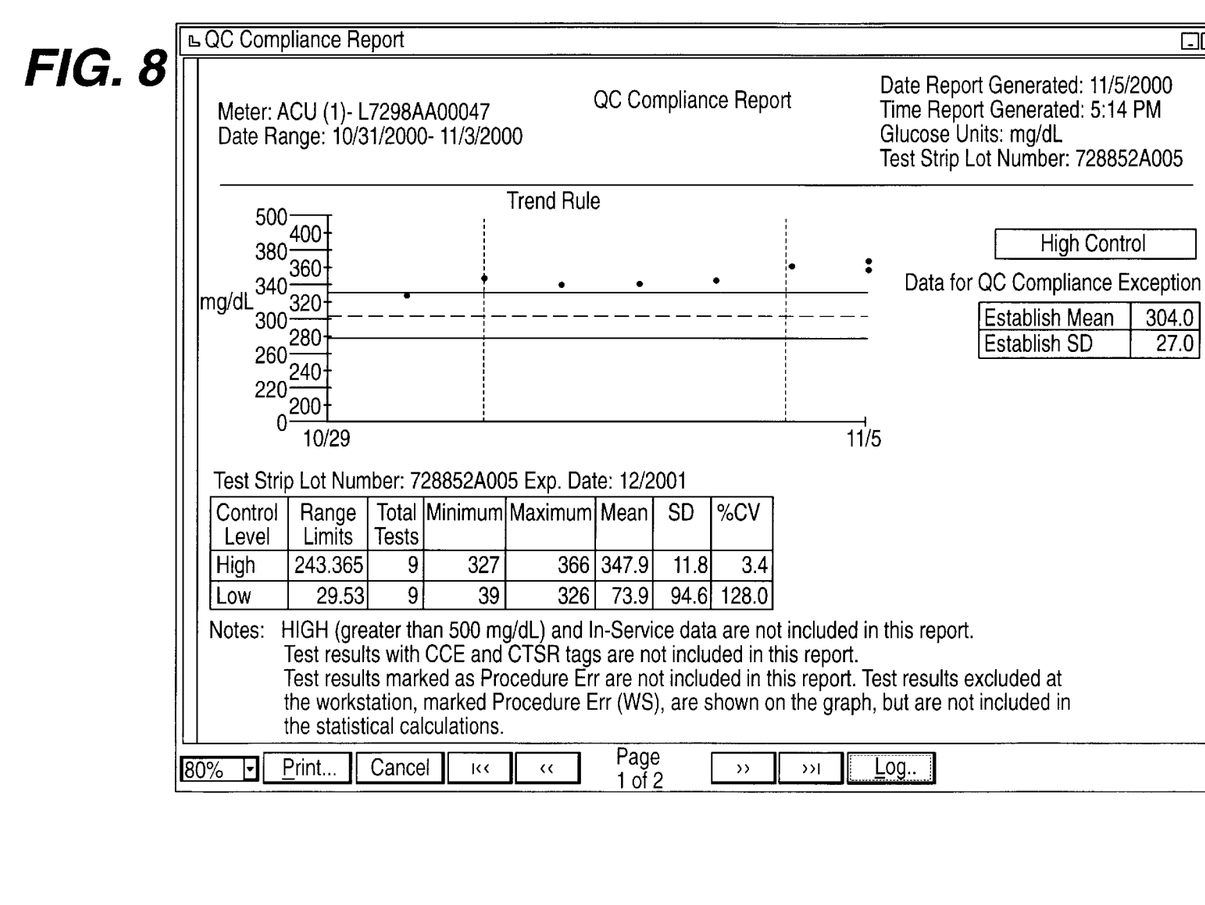
FIG. 8 is an example of an interface of displaying data included in a QC compliance report.

The QC Compliance Report summarizes the details of the exception and displays the data in a Levey-Jennings-type chart, where dotted lines 802, 804 mark the start and end points of the data in the exception.

In summary, the invention provides automated QC compliance checking for POC devices to verify that POC testing has been done properly.

The invention provides exception-based QC compliance to timely detect out-of-control testing. Further, the system and method provide the necessary reports to provide cost effective health care. The system does so through simple interfaces, and using data paths and method steps that are novel and enhance the quality of the data.

Other features and advantages of this invention should be apparent to a person of skill in the art who studies the above disclosure. Therefore, the scope of this invention should be limited only by the following claims.

What is claimed:

1. A method of providing automatic quality control (QC) compliance for point-of-care (POC) devices, comprising the steps of:

storing test results received from each of a plurality of POC devices, including an association with the operator of the POC device and/or a reagent used in obtaining the test results;

processing the results to detect any random and/or systemic exception from results that have previously been stored;

holding for review POC-collected patient results associated with a QC compliance exception;

delaying the reporting or transfer to an information system of potentially inaccurate patient results if said detecting step indicates the presence of a random or systematic exception; and automatically disabling a questionable POC device based on detection of a QC compliance exception.

2. A method of providing automatic quality control (QC) compliance for point-of-care (POC) devices, comprising the steps of:

storing test results received from each of a plurality of POC devices, including an association with the operator of the POC device and/or a reagent used in obtaining the test results;

processing the results to detect any random and/or systemic exception from results that have previously been stored;

holding for review POC-collected patient results associated with a QC compliance exception; and automatically invalidating a reagent lot that has established a QC exception by configuring a selected POC device.

3. A method of providing automatic quality control (QC) compliance for point-of-care (POC) devices, comprising the steps of:

storing test results received from each of a plurality of POC devices, including an association with the operator of the POC device and/or a reagent used in obtaining the test results;

processing the results to detect any random and/or systemic exception from results that have previously been stored;

holding for review POC-collected patient results associated with a QC compliance exception; and automatically invalidating an operator who has established a QC exception by configuring a selected POC device.

4. A method of providing automatic quality control (QC) compliance for point-of-care (POC) devices, comprising the steps of:

storing test results received from each of a plurality of POC devices, including an association with the operator of the POC device and/or a reagent used in obtaining the test results, and processing the results to detect any random and/or systemic exception from results that have previously been stored; and graphically presenting QC exceptions.

5. A method as claimed in claim 4 wherein the administrator can establish via an interface to a storage database the rules for defining the exceptions.

6. A method as claimed in claim 5 wherein the step of establishing rules includes a choice made on the interface between analyzing the data for random error or systemic error.

* * * * *